(12) United States Patent
Li et al.

(10) Patent No.: US 12,410,462 B1
(45) Date of Patent: Sep. 9, 2025

(54) METHOD FOR DETECTING BI-ALLELIC GENE EDITED CELLS BASED ON CRISPR/CAS12A TECHNOLOGY

(71) Applicant: Institute of Animal Science of Chinese Academy Of Agricultural Sciences, Beijing (CN)

(72) Inventors: Kui Li, Beijing (CN); Yulian Mu, Beijing (CN); Zhiguo Liu, Beijing (CN)

(73) Assignee: INSTITUTE OF ANIMAL SCIENCE OF CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 19/220,155

(22) Filed: May 28, 2025

(30) Foreign Application Priority Data

Dec. 4, 2024 (CN) .......................... 202411769301.0

(51) Int. Cl.
| | |
|---|---|
| *C12Q 1/6816* | (2018.01) |
| *C12N 9/22* | (2006.01) |
| *C12N 15/11* | (2006.01) |
| *C12Q 1/686* | (2018.01) |
| *G01N 21/64* | (2006.01) |

(52) U.S. Cl.
CPC ............ *C12Q 1/6816* (2013.01); *C12N 9/226* (2025.05); *C12N 15/11* (2013.01); *G01N 21/6428* (2013.01); *C12N 2310/20* (2017.05); *C12N 2320/10* (2013.01); *C12Q 1/686* (2013.01); *G01N 2021/6439* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 2016/0367702 A1* | 12/2016 | Hoge | .................. A61P 35/00 |
| 2024/0043840 A1* | 2/2024 | Sanjana | ............... C12N 15/111 |
| 2024/0124873 A1* | 4/2024 | Sanjana | ................ C12N 15/86 |

OTHER PUBLICATIONS

Gupta et al., CRISPR-Cas9 system:A new fangled dawn in gen editing. Life Sciences 232:116636 (Year: 2019).*
Issacs et al., RNA syntheic biology. Nature biotechnology 24(5) : 545 (Year: 2006).*
Ishibashi et al., Genome editing with the donor plasmid equipped with synthetic crRNA-target sequence. Scientific Reports 10:14120 (Year: 2020).*
Paul et al., CRISPR-Cas12a : Functional overview and applications. Biomedical Journal43:2-17 (Year: 2020).*
Wu et al. Target specificity of the CRISPR-Cas9 system. Quantitative Biology 2(2): 59-70 (Year: 2014).*
Xu Changjiang, et al., Establishment of pAPN Gene Knockout IPI-21 Cell Lines Mediated by CRISPR/Cas9 System, China Animal Husbandry & Veterinary Medicine, 2021, pp. 2283-2290, vol. 48 No. 7.
GenBank: NC_010455.5, Sus scrofa isolate TJ Tabasco breed Duroc chromosome 13, Sscrofa11.1, whole genome shotgun sequence, 2018.

* cited by examiner

*Primary Examiner* — Ethan C Whisenant
(74) *Attorney, Agent, or Firm* — Bayramoglu Law Offices LLC (57) ABSTRACT

A method for detecting bi-allelic gene edited cells based on CRISPR/Cas12a technology is provided. The method provides crRNA, a nucleotide sequence of which that binds target is SEQ ID NO: 6. The crRNA is transcribed from a transcription template in vitro; the transcription template is a product obtained by annealing a single stranded DNA molecule shown in SEQ ID NO: 10 and a single stranded DNA molecule shown in SEQ ID NO: 13. The method provides crRNA of CD71 gene and constructs a CRISPR/Cas12a system using the same for CRISPR/Cas12a detection, achieving the screening for CRISPR/Cas9 induced CD71 gene bi-allelic gene edited cells. This method is simple, easy, fast, and cost-effective for screening a large number of mutant cells.

18 Claims, 7 Drawing Sheets

Specification includes a Sequence Listing.

FIG. 1

CD71 Wild type sequence

CD71 Standard plasmid sequence

METHOD FOR DETECTING BI-ALLELIC GENE EDITED CELLS BASED ON CRISPR/CAS12A TECHNOLOGY

CROSS REFERENCE TO THE RELATED APPLICATIONS

This application is based upon and claims priority to Chinese Patent Application No. 202411769301.0, filed on Dec. 4, 2024, the entire contents of which are incorporated herein by reference.

SEQUENCE LISTING

The instant application contains a Sequence Listing which has been submitted in XML format via EFS-Web and is hereby incorporated by reference in its entirety. Said XML copy is named KJ0107S_SequenceListing.xml, created on Apr. 29, 2024, and is 20,697 bytes in size.

TECHNICAL FIELD

The present invention relates to the field of biological detection technology, specifically to a method for detecting bi-allelic gene edited cells based on clustered regularly interspaced short palindromic repeats (CRISPR)/CRISPR-associated protein 12a (Cas12a) technology.

BACKGROUND

CD71 gene, also known as transferrin receptor 1, is a type II transmembrane glycoprotein composed of 760 amino acids, which is located on chromosome 13 of pigs, with a size of approximately 51 kb. CD71 plays an important role in the field of cancer, and is expressed in a significant higher level in cancer tissues than that in normal tissues. By using specific antibodies to bind to CD71, abnormal cell proliferation can be effectively inhibited and apoptosis can be induced. Meanwhile, CD71 activates T cells and triggers non antibody dependent immune responses by participating in the signal transduction process of inducing T cells. Therefore, screening CD71 gene bi-allelic gene edited cells is of great significance for further studying their functions.

However, efficient and accurate detection of bi-allelic gene edited cells has always been a challenge. There are problems such as complex operation, time-consuming, and lower sensitivity in the existing detection methods. CRISPR/Cas12a system is a ribonucleic acid (RNA) guided DNA endonuclease-based technology, the core of which lies in formation of a complex between Cas12a protein and specifically designed CRISPR RNA (crRNA). This complex can accurately recognize and target DNA regions containing specific PAM sequences, and perform cleavage downstream the PAM sequence to produce DNA double strand breaks. After cleaving a target DNA, Cas12a protein enters an activated state and exhibits non-specific incidental cleavage activity, which can cleave nearby non target DNA molecules. This characteristic has been applied in CRISPR/Cas12a based nucleic acid detection systems and has great potential in the field of mutation detection.

SUMMARY

The technical problem solved by the present invention is how to quickly and accurately identify CRISPR/Cas9 induced bi-allelic gene edited cells.

In order to solve the above technical problem, in the first aspect, the present invention provides a crRNA, a nucleotide sequence of which that binds a target is SEQ ID NO: 6.

In the above, the target of the CD71 gene described above is located in the third exon of a pig CD71 gene.

In the crRNA described above, said crRNA is transcribed from a transcription template in vitro;

the transcription template is a product obtained by annealing a single stranded DNA molecule shown in SEQ ID NO: 10 and a single stranded DNA molecule shown in SEQ ID NO: 13.

In the crRNA described above, a nucleotide sequence of said crRNA is SEQ ID NO: 16.

In the second aspect, the present invention provides a product including the crRNA as described in the first aspect.

The product described above also includes a Cas12a protein.

In the embodiments of the present invention, specifically a LbCas12a protein.

The product described above also includes a primer pair for specific amplification of the target; the primer pair consists of a single stranded DNA molecule as shown in SEQ ID NO: 2 and a single stranded DNA molecule as shown in SEQ ID NO: 3.

The product described above also includes a single stranded DNA probe, respectively, the single stranded DNA probe is labeled with different groups at both ends;

and/or the groups are fluorescent groups, quenching groups, and/or a biotin.

The above described single stranded DNA probe is a single stranded DNA with a length of 5-50 nt and rich in AT bases.

In the embodiments of the present invention, the single stranded DNA probe in a CRISPR/Cas12a fluorescence detection system is 6-FAM-TTATT-BHQ1; the single stranded DNA probe in a CRISPR/Cas12a colloidal gold test strip detection system is 6-FAM-TTTTTTTATTTTTT (SEQ ID NO: 17)-C6Biotin.

The products described above are kits, test strips, or fluorescence detection systems.

In the third aspect, the present invention provides any of the following substances:

A1) the Cas12a protein and the crRNA described in the second aspect, or a complex formed by the two;

A2) the primer pairs as described in the second aspect.

In the fourth aspect, the present invention provides a use of crRNA as described in the first aspect or the product as described in the second aspect in any of the following:

B1) detection or auxiliary detection of bi-allelic gene editing of a CD71 gene;

B2) preparation of products for detecting or assisting bi-allelic gene editing of a CD71 gene;

B3) detection or auxiliary detection of bi-allelic gene edited samples of a CD71 gene;

B4) preparation of products for detecting or auxiliarily detecting bi-allelic gene edited samples of a CD71 gene.

Or, the present invention provides a method for detecting or assisting bi-allelic gene edited samples of a CD71 gene, including the following steps:

C1) using a nucleic acid of a sample to be tested as a template, a polymerase chain reaction (PCR) amplification is performed using a primer pair consisting of a single stranded DNA molecule as shown in SEQ ID NO: 2 and a single stranded DNA molecule as shown in SEQ ID NO: 3 to obtain a PCR product;

C2) preparing a CRISPR/Cas12a detection system including the following components: the PCR product, the Cas12a protein as described in the second aspect, the crRNA as described in the second aspect, and the single stranded DNA probe as described in the second aspect;

C3) reacting the CRISPR/Cas12a detection system and detecting reaction products to identify whether the sample to be tested is bi-allelic gene edited samples of the CD71 gene.

In the above, the bi-allelic gene edited samples of said CD71 gene are obtained by gene editing in a target region shown in SEQ ID NO: 7 of the third exon of the CD71 gene in the sample, so that the target region on both homologous chromosomes of the sample undergo gene editing. The above methods are for purposes of non-diagnosis of a disease.

In the above, said sample to be tested is a cell or an organism.

In the embodiments of the present invention, as an example, the cell is a cell with CD71 gene edited, can be cells with a wild-type CD71 gene, CD71 gene mono-allelic gene edited cells, and/or CD71 gene bi-allelic gene edited cells.

The above described wild-type cells of CD71 gene are cells with the CD71 gene on two homologous chromosomes that have not undergo gene editing;

the above described CD71 gene mono-allelic gene edited cells involve gene editing of a target region (SEQ ID NO: 7) in the third exon of the CD71 gene on one homologous chromosome, and remaining the CD71 gene unchanged on the other homologous chromosome, in the cell;

the above described CD71 gene bi-allelic gene edited cells involve gene editing of a target region (SEQ ID NO: 7) in the third exon of the CD71 gene on two homologous chromosomes in the cell.

The present invention provides a crRNA of a CD71 gene, and constructs a CRISPR/Cas12a system for CRISPR/Cas12a detection using the same, to achieve the screening of CRISPR/Cas9 induced CD71 gene bi-allelic gene edited cells. This method is simple, easy, fast, and cost-effective for screening a large number of mutant cells.

DETAILED DESCRIPTION OF THE EMBODIMENTS

The present invention is further described in detail as below in conjunction with specific embodiments. The provided embodiments are only intended to illustrate the present invention and not to limit its scope. The Examples provided below can serve as a guide for those skilled in the art to further improve and do not in any way limit the present invention.

The experimental methods in the following examples, unless otherwise specified, are all conventional methods, and carried out according to the techniques or conditions described in the literature in the art or according to the product manual. All the materials, reagents, etc. used in the following examples are commercially available unless otherwise specified.

The present invention is described in conjunction with specific examples as follows, these examples are only exemplary and are not intended to limit the scope of the present invention. Unless otherwise specified, the examples are carried out under conventional experimental conditions, such as those in the Sambrook et al. Molecular Cloning: a Laboratory Manual (Sambrook J & Russell D W, Molecular Cloning: a Laboratory Manual, 2001), or under conditions recommended by the manufacturer's instructions.

The main reagents used in the following examples:

LbCas12a protein (EDE0005) was purchased from Guangzhou Edgene Technology Co., Ltd;

10×LbCas12a Cleavage Buffer (EDE0005-B) was purchased from Guangzhou Edgene Technology Co., Ltd;

KOD enzyme (KFX-101) was purchased from Biolink (Beijing) Biotechnology Co., Ltd;

*Escherichia coli* DH5a competent cells (B528413-0100) were purchased from Sango Biotech (Shanghai) Co., Ltd;

CloneSmarter TOPO cloning vector kit (C5865-50) was purchased from Zhongmei Taihe Biotechnology (Beijing) Co., Ltd;

EndoFree Plasmid Midi Kit (CW2105S) was purchased from Jiangsu Cowin Biotech Co., Ltd.

PCR primers were synthesized by Beijing Tsingke Biotechnology Co., Ltd;

T7 in vitro transcription kit (AM1354) was produced by Invitrogen company;

RNA purification and recovery kit (12183018A) was produced by Invitrogen company;

Single stranded DNA fluorescent probe was synthesized by Sango Biotech (Shanghai) Co., Ltd;

Single stranded DNA colloidal gold probe (EDN-THD02) was purchased from Guangzhou Edgene Technology Co., Ltd;

CRISPR Cas12/13 HybriDetect test strip (JY0301) was purchased from Guangzhou Edgene Technology Co., Ltd;

Rnase Free Water (9012) was purchased from Beijing Liuhetong Economic and Trade Co., Ltd.

The main instruments are as follows:

PCR instrument (BIO-RAD, C1000 Touch™);

Desktop high-speed refrigerated centrifuge (Thermo Scientific, Heraeus Multifuge X1R);

Bacterial incubator (SANYO, MIR-254);

Constant temperature water bath (Changzhou Nuoji Instrument Co., Ltd., HHS-21-4);

Vortex oscillator (Stuart equipment, SA8);

Electronic weighing balance (Sartorius SQP, Sartorius Scientific Instrument Co., Ltd.);

Gel imaging system (BIO-RID, Universal Hood II);

Fluorescent quantitative PCR instrument (Thermo Scientific, QuantStudio)™ 5).

Porcine ileal Epithelial Cells (IPI-21) are recorded in the following literature: Xu Changjiang, Wang Xiaopeng, Xu Kui, Zhang Xiuling, Xiang Guangming, Zhao Haiquan, Mou Yulian, Lin Xiao, Li Kui Construction of an IPI-2I cell line with pAPN gene knockout using CRISPR/Cas9 editing system. China Animal Husbandry & Veterinary Medicine, 2021, 48 (7): 2282-2290.

Example 1: Design of PCR-CRISPR/Cas12a Nucleic Acid Detection System

1. Construction of Standard Plasmids

Wild-type (WT) DNA was extracted from porcine ileal epithelial cells (IPI-21), and primers (primer sequence shown in Table 1) for amplification of a sequence containing sgRNA in the third exon of CD71 gene (GenBank: NC-010455.5) were designed, in which the sequence of a sgRNA target was GTAGCCAATCATAAATCCTA (SEQ ID NO: 1). The amplified fragment has a size of 591 bp, and its PCR amplification system was shown in Table 2.

TABLE 1

Primer Sequence

| Name | Sequence (5'-3') | Name of corresponding sequences |
|---|---|---|
| CD71-F | TGAGGATTCAAGGTAGGCT | SEQ ID NO: 2 |
| CD71-R | CTGATGCCCTTGTGGATAG | SEQ ID NO: 3 |

TABLE 2

PCR Amplification System

| components | Volume |
|---|---|
| Wide type cellular DNA sample | 2.0 μL |
| CD71-F primer | 0.4 μL |
| CD71-R primer | 0.4 μL |
| KOD enzyme | 0.4 μL |
| dNTP | 4.0 μL |
| Buffer | 10.0 μL |
| ddH$_2$O | 2.8 μL |
| Total | 20.0 μL |

PCR reaction procedure: predenature at 94° C. for 2 minutes; denaturature at 94° C. for 10 seconds, anneal at 60° C. for 30 seconds, extend at 68° C. for 36 seconds, 36 cycles; extend at 72° C. for 5 minutes.

Figure 1:
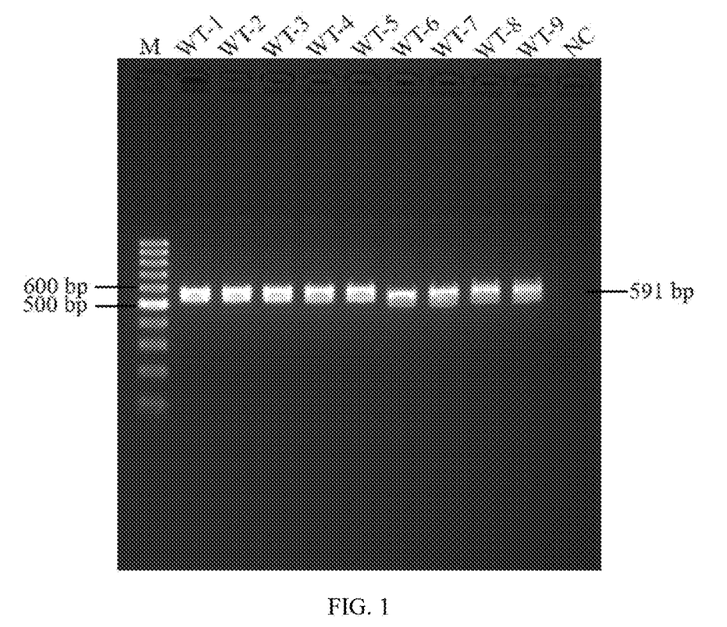
FIG. 1 shows electrophoresis results of PCR amplification of wild-type porcine ileal epithelial cells in Example 1 of the present invention.

Agarose gel electrophoresis was performed after completion of PCR amplification. The electrophoresis result was shown in FIG. 1, in which M was a GsDL1002 DNA Marker of 1000 bp; NC was a negative control; WT-1 to WT-9 were all DNA samples by PCR amplification of wild-type porcine ileal epithelial cells, respectively. It could be seen that the PCR products were successfully amplified, and a single band of approximately 591 bp appeared at the expected position.

Figure 2:
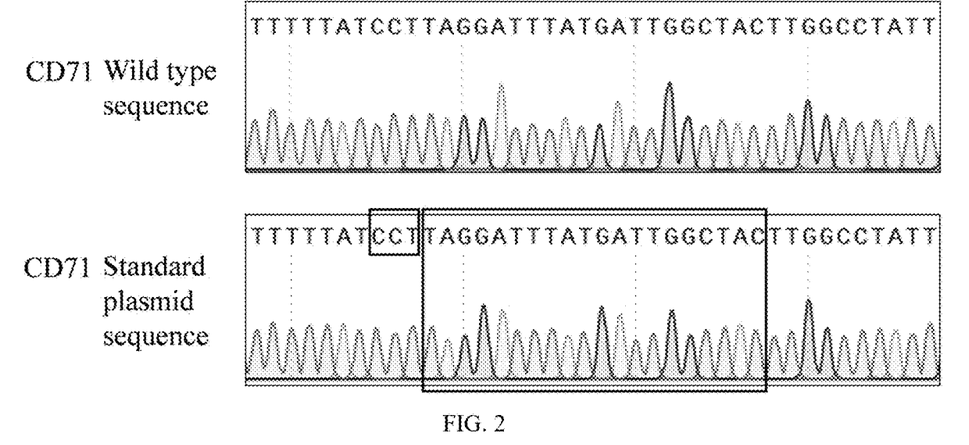
FIG. 2 shows the sequencing results of the standard plasmid of wild-type porcine CD71 gene in Example 1 of the present invention, including TTTTTATCCTTAGGATTTATGATTGGCTACTTGGCCTATT shown in SEQ ID NO: 18.

The PCR product was purified by gel recovery, and the purified product was cloned and ligated into a pClone-EZ-TOPO vector (Zhongmei Taihe Biotechnology (Beijing) Co., Ltd., C5865-50) through TA cloning. The ligated product was sequenced and validated to obtain a wild-type standard plasmid pClone EZ-TOPO-WT of the pig CD71 gene. The plasmid sequencing results were shown in FIG. 2. The selected blue area represented a reverse complementary sequence of the sgRNA target shown in SEQ ID NO: 1, and the selected area with red box represented a PAM sequence.

2. Design of crRNA Target

Based on the DNA sequence within 40 bp range of upstream and downstream sgRNA in the third exon of pig CD71 gene, PAM sequences marked by TTN or TTTN were searched, and downstream of the PAM sequences were extended 20 bp-25 bp as candidate target sites for CRISPR/Cas12a system recognition. Then, three candidate target sites were designed according to the rules such as GC content in a sequence and sequence complementarity, and designated as crRNA-T1 (SEQ ID NO: 4), crRNA-T2 (SEQ ID NO: 5), crRNA-T3 (SEQ ID NO: 6) respectively (see Table 3 for candidate target site sequences).

The sequence TTTTTTATCCTTAGGATTTATGATTGGCTAC covered by the above three candidate target sites and sgRNA target site is a sequence (SEQ ID NO: 7) that crRNA targeted for cleavage.

TABLE 3

Candidate Target Site Sequences

| Name | Sequences (5'-3')(The sequences with underline are PAM sequences) | Length | Name of corresponding sequences |
| --- | --- | --- | --- |
| crRNA-T1 | TTTATCCTTAGGATTTATGATTGG | 24 bp | SEQ ID NO: 4 |
| crRNA-T2 | TTTTTTATCCTTAGGATTTATGA | 23 bp | SEQ ID NO: 5 |
| crRNA-T3 | TTTTTTATCCTTAGGATTTATGATTGG | 27 bp | SEQ ID NO: 6 |

3. Preparation of In Vitro Transcription Templates of Specific crRNA

Based on candidate target site sequences, a T7 promoter sequence (TAATACGACTCACTATAGGG, SEQ ID NO: 21) and a crRNA repeat region template sequence (TAATTTCTACTAAGTGTAGAT, SEQ ID NO: 22) were added respectively to form in vitro transcription template forward strand DNA sequences for specific crRNA, crRNA-T7-F1 (SEQ ID NO: 8), crRNA-T7-F2 (SEQ ID NO: 9), and crRNA-T7-F3 (SEQ ID NO: 10).

According to complementary pairing of forward strand DNA sequences, reverse strand DNA sequences crRNA-T7-R1 (SEQ ID NO: 11), crRNA-T7-R2 (SEQ ID NO: 12), and crRNA-T7-R3 (SEQ ID NO: 13) were formed.

The prepared system was placed in a PCR instrument (BIO-RAD, C1000 Touch™), incubated at 95° C. for 10 minutes, then the PCR instrument was immediately turn off, the double strand was allowed to cool naturally at room temperature for 90 minutes, followed by incubation on ice for 5 minutes. The annealed product can be used for in vitro transcription of crRNA.

4. In Vitro Transcription of Specific crRNA

An in vitro transcription system as shown in Table 6 of specific crRNA was prepared using a T7 in vitro transcription kit (Invitrogen, AM1354).

TABLE 4

Forward and Reverse Strand DNA Sequences of in Vitro Transcription Template for Specific crRNA

| Name | Sequence(5'-3') | Length | Name of corresponding sequences |
| --- | --- | --- | --- |
| crRNA-T7-F1 | TAATACGACTCACTATAGGGTAATTTCTACTA AGTGTAGATTCCTTAGGATTTATGATTGG | 61 bp | SEQ ID NO: 8 |
| crRNA-T7-F2 | TAATACGACTCACTATAGGGTAATTTCTACTA AGTGTAGATTTATCCTTAGGATTTATGA | 61 bp | SEQ ID NO: 9 |
| crRNA-T7-F3 | TAATACGACTCACTATAGGGTAATTTCTACTA AGTGTAGATTTATCCTTAGGATTTATGATTGG | 64 bp | SEQ ID NO: 10 |
| crRNA-T7-R1 | CCAATCATAAATCCTAAGGAATCTACACTTA GTAGAAATTACCCTATAGTGAGTCGTATTA | 61 bp | SEQ ID NO: 11 |
| crRNA-T7-R2 | TCATAAATCCTAAGGATAAAATCTACACTTAG TAGAAATTACCCTATAGTGAGTCGTATTA | 61 bp | SEQ ID NO: 12 |
| crRNA-T7-R3 | CCAATCATAAATCCTAAGGATAAATCTACACT TAGTAGAAATTACCCTATAGTGAGTCGTATTA | 64 bp | SEQ ID NO: 13 |

Single strands of forward and reverse strand DNA were synthesized, respectively, in vitro transcription templates of specific crRNA were prepared by annealing, and a system for annealing reaction as shown in Table 5 was prepared.

TABLE 5

Annealing Reaction System

| Components | Volume |
| --- | --- |
| Forward strand DNA(100 µM) | 2.0 µL |
| Reverse strand DNA(100 µM) | 2.0 µL |
| ddH$_2$O | 16.0 µL |
| Total volume | 20.0 µL |

TABLE 6

In Vitro Transcription of Specific crRNA

| Components | Volume |
| --- | --- |
| Nuclease-Free Water | 16.0 µL |
| NTP buffer Mix | 10.0 µL |
| Template | 2.0 µL |
| T7 RNA Polymerase Mix | 2.0 µL |
| Total volume | 30.0 µL |

The transcription system was placed and incubated overnight in a 37° C. incubator. RNA purification recovery kit (Invitrogen, 12183018A) was used for crRNA recovery. The recovered crRNA sequences were shown in Table 7.

TABLE 7 crRNA Sequence

| Name | Sequence(5'-3') | Length | Names of corresponding sequence |
|------|-----------------|--------|---------------------------------|
| crRNA-F1 | UAAUUUCUACUAAGUGUAGAUUCCUUAGG AUUUAUGAUUGG | 41 bp | SEQ ID NO: 14 |
| crRNA-F2 | UAAUUUCUACUAAGUGUAGAUUUUAUCCU UAGGAUUUAUGA | 41 bp | SEQ ID NO: 15 |
| crRNA-F3 | UAAUUUCUACUAAGUGUAGAUUUAUCCUU AGGAUUUAUGAUUGG | 44 bp | SEQ ID NO: 16 |

5. Establishment of PCR-CRISPR/Cas12a Nucleic Acid Detection System (1) CRISPR/Cas12a fluorescence detection system was shown in Table 8 below:

TABLE 8

CRISPR/Cas12a Fluorescence Detection System

| Components | Volume |
|------------|--------|
| 10 × LbCas12a Cleavage Buffer | 3.0 μL |
| LbCas12a(1 μM) | 1.0 μL |
| crRNA(500 nM) | 2.0 μL |
| DNA Probe(2 μM) | 6.0 μL |
| Enzyme free sterile water | 17.0 μL |
| PCR products | 1.0 μL |
| Total volume | 30.0 μL |

The above described DNA probe is a single stranded DNA probe double labeled with a 6-FAM group and a BHQ group, which is 6-FAM-TTATT-BHQ1.

The above described PCR products were obtained by PCR amplification using the standard plasmid pClone EZ-TOPO-WT as a DNA template and CD71-F/CD71-R primers. The above described crRNAs were crRNA-F1, crRNA-F2, and crRNA-F3, respectively.

crRNA-F1, crRNA-F2, and crRNA-F3 detection systems were prepared respectively according to the above systems, with four technical replicates set up for each detection system, and a crRNA free system set up as a negative control (NC).

The prepared detection systems were separately reacted at 37° C. in a fluorescence quantitative PCR instrument (Thermo Scientific, QuantStudio™ 5), with fluorescence intensity set to be detected every 30 seconds for a total of 120 times.

Figure 3:
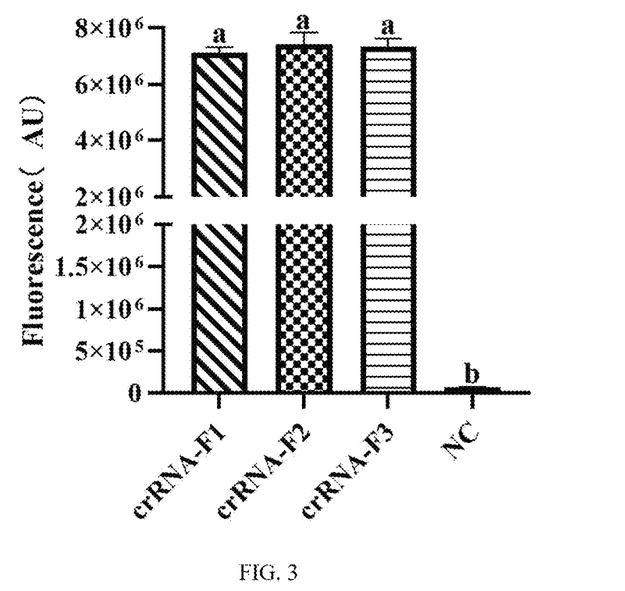
FIG. 3 shows the fluorescence intensity detection results of activities of a crRNA targeting the sequence of wild-type porcine CD71 gene in Example 1 of the present invention. Different lowercase letters indicate existence of significant differences (P<0.05).

Results were shown in FIG. 3, the fluorescence intensities of crRNA-F1, crRNA-F2, and crRNA-F3 groups all were significantly increased ($P<0.05$) compared with the negative control group, indicating that crRNA-F1, crRNA-F2, and crRNA-F3 all have targeted cleavage effects on the wild-type sequence of CD71 gene (SEQ ID NO: 7).

(2) CRISPR/Cas12a colloidal gold test strip detection system was shown in Table 9:

TABLE 9

CRISPR/Cas12a colloidal gold test strip detection system

| Components | Volume |
|------------|--------|
| 10 × LbCas12a Cleavage Buffer | 3.0 μL |
| LbCas12a (1 μM) | 1.0 μL |
| crRNA (500 nM) | 2.0 μL |
| colloidal gold probe (2 μM) | 6.0 μL |
| Enzyme free sterile water | 37.0 μL |
| PCR products | 1.0 μL |
| Total volume | 50.0 μL |

The above described colloidal gold probe was a single stranded colloidal gold probe double labeled with a Biotin group and a 6-FAM group, which is 6-FAM-TTTTTTTAT-TTTTTT (SEQ ID NO: 17)-C6Biotin.

The above described PCR products were obtained by PCR amplification using the standard plasmid pClone-EZ-TOPO-WT as a DNA template and CD71-F/CD71-R primers.

The above described crRNAs was crRNA-F1, crRNA-F2, and crRNA-F3, respectively. crRNA-F1, crRNA-F2, and crRNA-F3 detection systems (referred to as WT in Figures) were prepared according to the above system, with four technical replicates set up for each detection system, and a crRNA free system set up as a negative control (NC).

The prepared detection systems were reacted in a PCR instrument (BIO-RAD, C1000 Touch™) at 37° C. for 30 minutes to obtain reaction products. After the reactions were completed, the pad ends of test strips were inserted into the reaction products in the reaction tubes, and test results were read after the reading area is fully immersed.

Figure 4:
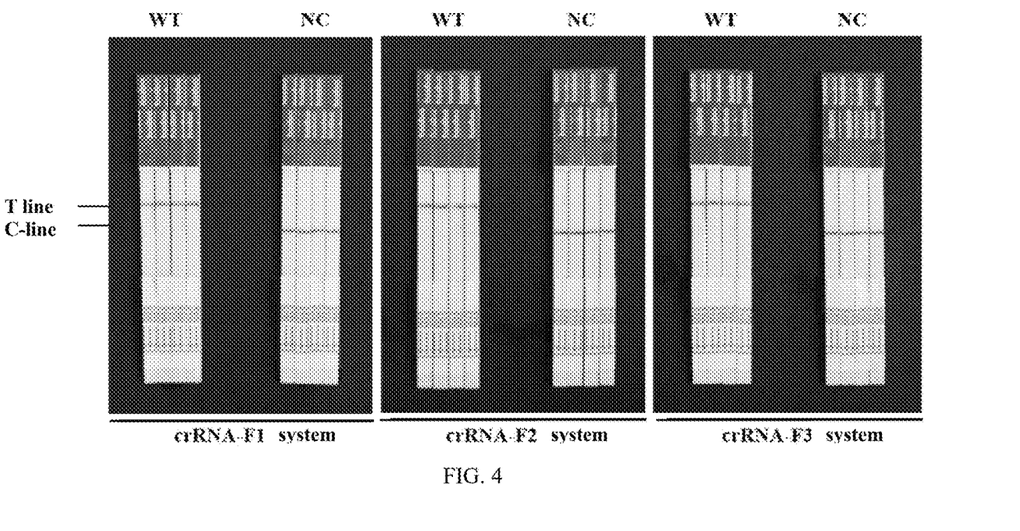
FIG. 4 shows colloidal gold test strip detection results of activities of a crRNA targeting the sequence of wild-type porcine CD71 gene in Example 1 of the present invention.

Results were shown in FIG. 4, compared with NC (negative result), crRNA-F1, crRNA-F2, and crRNA-F3 all can specifically recognize the wild-type sequence of the CD71 gene (SEQ ID NO: 7), i.e., the test strip showed a T-line coloration and represented a positive result; and the negative control group only showed C-line coloration and presented a negative result.

Example 2: Detection and Analysis of Monoclonal Cell Samples in CRISPR/Cas12a Nucleic Acid Detection System PCR Cas12a detection system provided by the present invention was used to screen CD71 gene bi-allelic gene edited cells from monoclonal cells.

The monoclonal cells in the Examples of the present invention were gene edited cells obtained by CRISPR/Cas9 gene editing of porcine ileal epithelial cells (IPI-21), in which the target of sgRNA is GTAGCCAATCAT-AAATCCTA (SEQ ID NO: 1).

1. Screening of crRNA (1) Amplification of a target sequence of Cas9/sgRNA target site Monoclonal cells were 2-1 #, 2-10 #, 2-12 #, and 2-30 #; it was known that 2-10 #and 2-12 #were CD71 gene bi-allelic gene edited cells; 2-1 #was wild-type cell; 2-30 #were CD71 gene monoallelic gene edited cells.

PCR amplification was performed using the lysate products of each of monoclonal cells as DNA templates, and CD71-F and CD71-R. The PCR system and reaction procedure were described in 1 of Example 1, to obtain PCR amplification products.

(2) PCR-CRISPR/Cas12a Nucleic Acid Detection

According to the system shown in Table 8 of Example 1, the above described PCR amplification products and crRNA were used to prepare crRNA-F1, crRNA-F2, and crRNA-F3 detection systems. Four technical replicates were set up for each detection system, and a crRNA free system was set up as a negative control (NC).

The prepared detection system was reacted in a fluorescence quantitative PCR instrument (Thermo Scientific, QuantStudio™5) at 37° C. and the fluorescence intensity was set to be detected every 30 seconds for a total of 120 times.

Figure 5A:
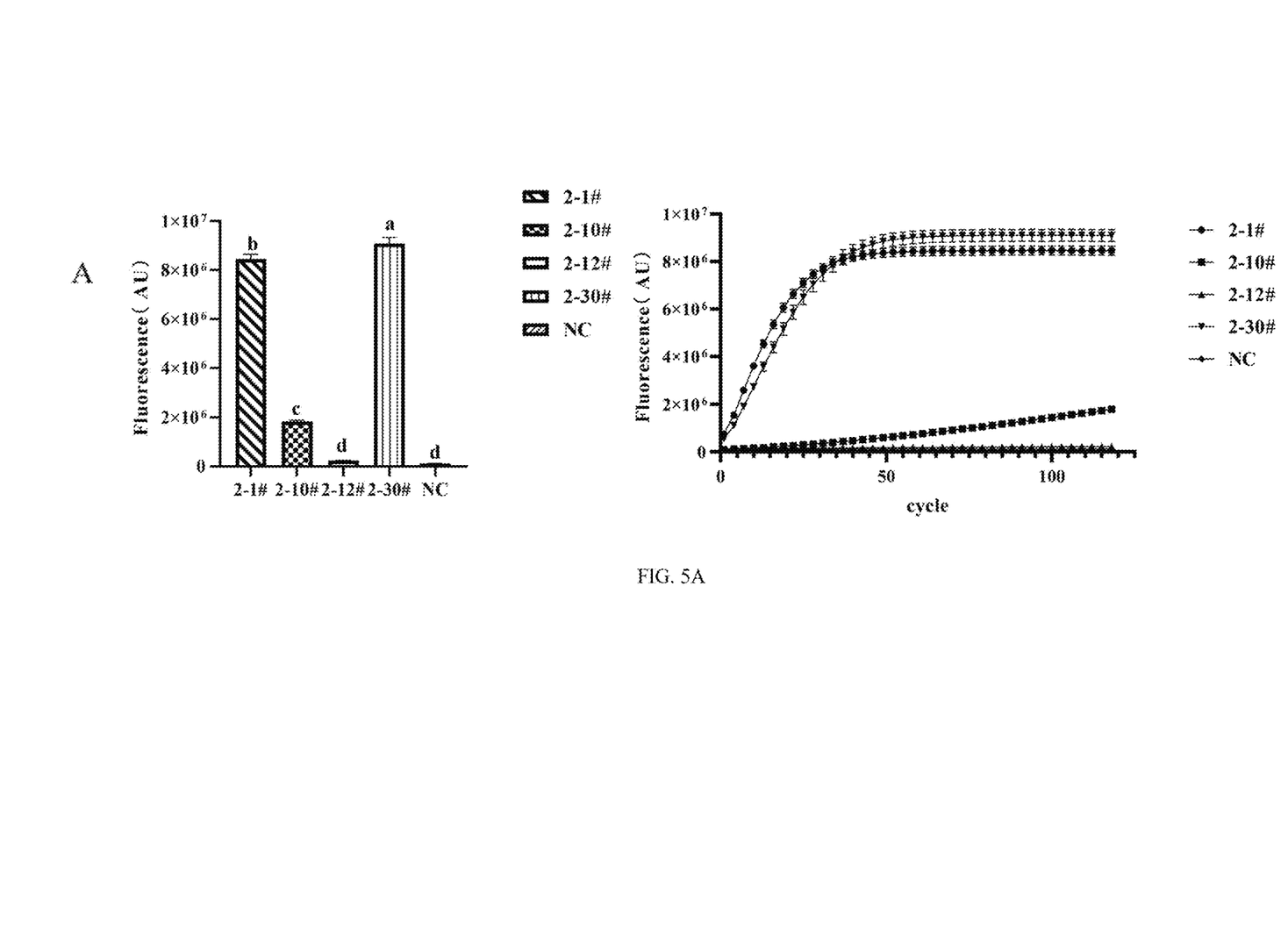
FIGS. 5A-5C show the detection results of CD71 gene edited cells in a portion of monoclonal cells by crRNA-F1, crRNA-F2, and crRNA-F3 fluorescence reporter systems in Example 2 of the present invention. Different lowercase letters indicate existence of significant differences (P<0.05).
Figure 5B:
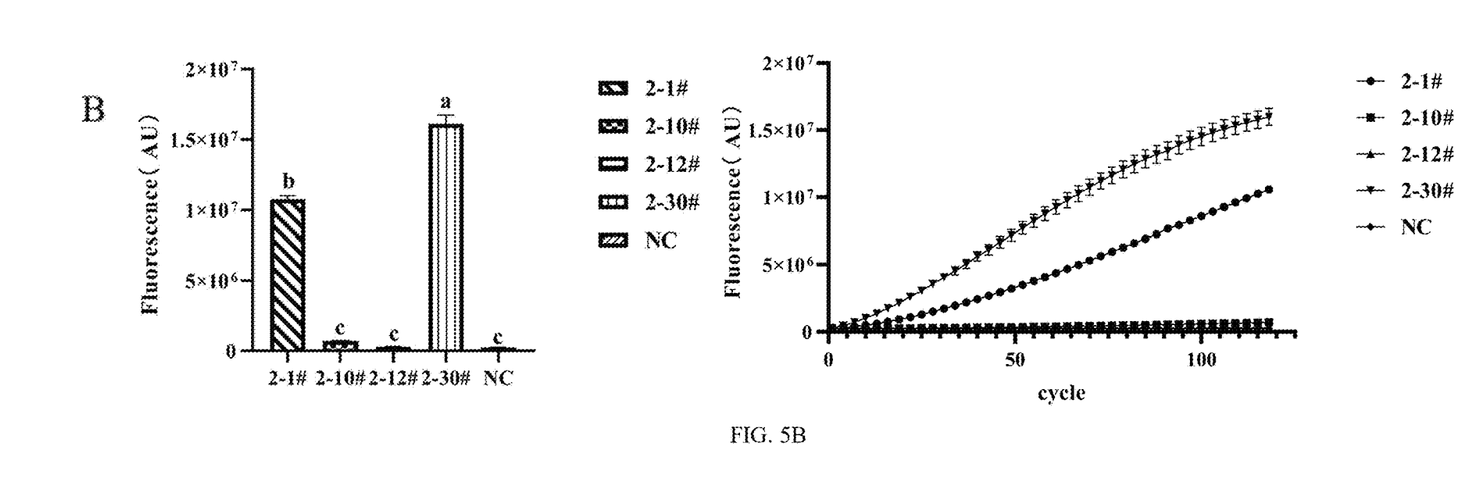
Figure 5C:
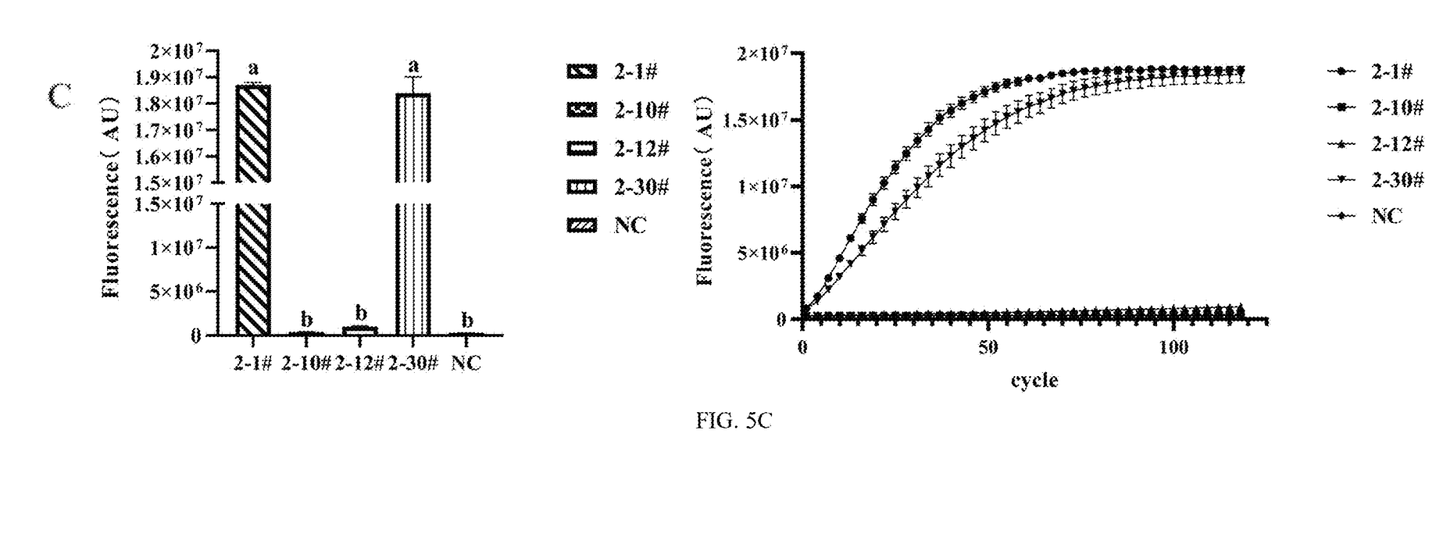

Results were shown in FIGS. 5A-5C, FIG. 5A: detection results of crRNA-F1 system; FIG. 5B: detection results of CrRNA-F2 system; FIG. 5C: detection results of CrRNA-F3 system; CrRNA-F1 could identify CD71 gene bi-allelic gene edited cell samples (2-10 #and 2-12 #), but the fluorescence intensity of the 2-10 #monoclonal cell sample still showed significant difference (P<0.05) compared to the negative control, which may be due to its non-specific recognition of the mutant sequence. CrRNA-F2 could identify CD71 gene bi-allelic gene edited cell samples (2-10 #and 2-12 #), but has a slower reaction, as shown by the fluorescence curve, which could result in limitation of its detection efficiency in practical applications. In contrast, crRNA-F3 detection performed well, with no significant difference in fluorescence intensity between the detected bi-allelic gene edited cells and the negative control group (P>0.05), and could identify CD71 gene bi-allelic gene edited cell samples (2-10 #and 2-12 #); and has a fast reaction speed and strong stability, which helped ensure detection efficiency and accuracy in practical applications. Therefore, crRNA-F3 was chosen for subsequent detection.

2. Establishment of PCR-CRISPR/Cas12a Nucleic Acid Detection System and Method (1) PCR Amplification DNA was extracted from a sample to be tested as a template, and PCR amplification was performed using CD71-F and CD71-R primers to obtain PCR amplification products.

(2) CRISPR/Cas12a Detection

1) CRISPR/Cas12a Fluorescence Detection

According to the system shown in Table 8, a CRISPR/Cas12a fluorescence detection system was prepared using the above described PCR amplification products and crRNA-F3 to obtain the CRISPR/Cas12a detection system;

Four technical replicates were set up for the above described detection system and a negative control (NC) without crRNA was set up.

The prepared detection system was reacted in a fluorescence quantitative PCR instrument (Thermo Scientific, QuantStudio)™ 5) at 37° C. for 60 minutes.

The reaction products of the above fluorescence detection system were detected real time for fluorescence intensity using a fluorescence quantitative PCR instrument (Thermo Scientific, QuantStudio™ 5).

If the fluorescence intensity of the reaction product in a CRISPR/Cas12a detection system is not significantly higher than that of the reaction product in the negative control system (P>0.05), then the sample to be tested is a CD71 gene bi-allelic gene edited sample or a candidate for CD71 gene bi-allelic gene edited sample; if the fluorescence intensity of the reaction product in the CRISPR/Cas12a detection system is significantly higher than that of the reaction product in the negative control system (P<0.05), then the sample to be tested is not a CD71 gene bi-allelic gene edited sample or not a candidate for CD71 gene bi-allelic gene edited sample.

The only difference between the above described negative control system and the CRISPR/Cas12a detection system is the absence of crRNA.

2) CRISPR/Cas12a Test Strip Detection

A CRISPR/Cas12a colloidal gold test strip detection system was prepared by the above described PCR amplification products and crRNA-F3 according to the system shown in Table 9, to obtain a CRISPR/Cas12a detection system;

Four technical replicates were set up for the above detection system and a negative control (NC) without crRNA was set up.

The prepared detection systems were reacted in a PCR instrument (BIO-RAD, C1000 Touch™) at 37° C. for 30 minutes to obtain reaction products.

CRISPR/Cas12a colloidal gold test strip is used to detect the reaction products. If T-line of the reaction product does not show coloration (negative), then the sample to be tested is a CD71 gene bi-allelic edited sample or is a candidate for a CD71 gene bi-allelic edited sample; if the T-line of the reaction product shows coloration or both T-line and C-line show coloration (positive), then the sample to be tested is not a CD71 gene bi-allelic edited sample or not a candidate for a CD71 gene bi-allelic edited sample.

The above samples are cells. In the above, the CD71 gene bi-allelic gene edited cells, in which a target region (SEQ ID NO: 7) in the third exon of the CD71 gene on two homologous chromosomes was gene edited compared to that of the CD71 gene in cells without being gene edited.

Non-CD71 gene Bi-allelic gene edited cells are CD71 gene mono-allelic gene edited cells or CD71 gene wild-type cells;

The above described CD71 gene wild-type cells are cells in which CD71 genes on two homologous chromosomes have not undergone gene editing;

The above described CD71 gene mono-allelic gene edited cells involve gene editing of a target region (SEQ ID NO: 7) in the third exon of the CD71 gene on one homologous chromosome compared to the CD71 gene in cells without gene editing, and remaining the CD71 gene unchanged on the other homologous chromosome compared to the CD71 gene in cells without gene editing.

Example 3: Applications of crRNA-F3 Nucleic Acid Detection System in Detection and Analysis of Monoclonal Cell Samples The monoclonal cells in the Examples of the present invention were gene edited cells obtained by CRISPR/Cas9 gene editing of porcine ileal epithelial cells (IPI-21), where the target of sgRNA was GTAGCCAATCATAAATCCTA (SEQ ID NO: 1).

1. CRISPR/Cas12a Fluorescence Detection

According to the method described in 2 of Example 2, CRISPR/Cas12a fluorescence detection was performed by crRNA-F3 nucleic acid detection method using a PCR product of monoclonal cell samples as a detection template.

The monoclonal cell samples were 2-7 #, 2-25 #, 2-26 #, 2-28 #, 2-29 #, 2-31 #, 1-28 #, 2-13 #, and 2-17 #, respectively.

Figure 6:
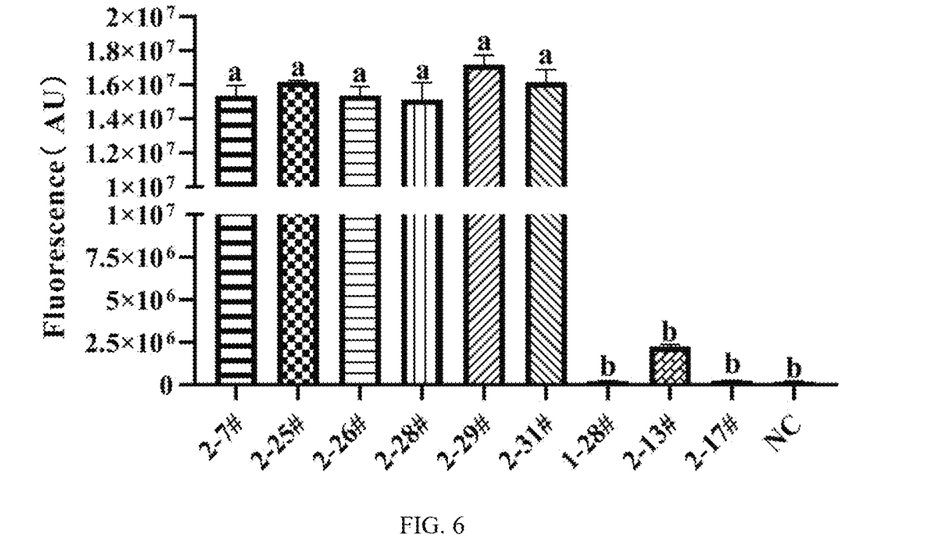
FIG. 6 shows the detection results of CD71 gene edited cells in monoclonal cells by crRNA-F3 fluorescence reporter system in Example 3 of the present invention. Different lowercase letters indicate existence of significant differences (P<0.05).

Results were shown in FIG. 6, the fluorescence intensities of 2-7 #, 2-25 #, 2-26 #, 2-28 #, 2-29 #, and 2-31 #were significantly increased compared to NC (P<0.05), indicating that they were not CD71 gene bi-allelic gene edited cells; there was no significant difference (P>0.05) in fluorescence intensity of 1-28 #, 2-13 #, 2-17 #compared to NC, they were CD71 gene bi-allelic gene edited cells.

2. CRISPR/Cas12a Test Strip Detection

According to the method described in 2 of Example 2, CRISPR/Cas12a test strip detection was performed by a crRNA-F3 nucleic acid detection method using a PCR product of the monoclonal cell sample as a detection template.

Figure 7:
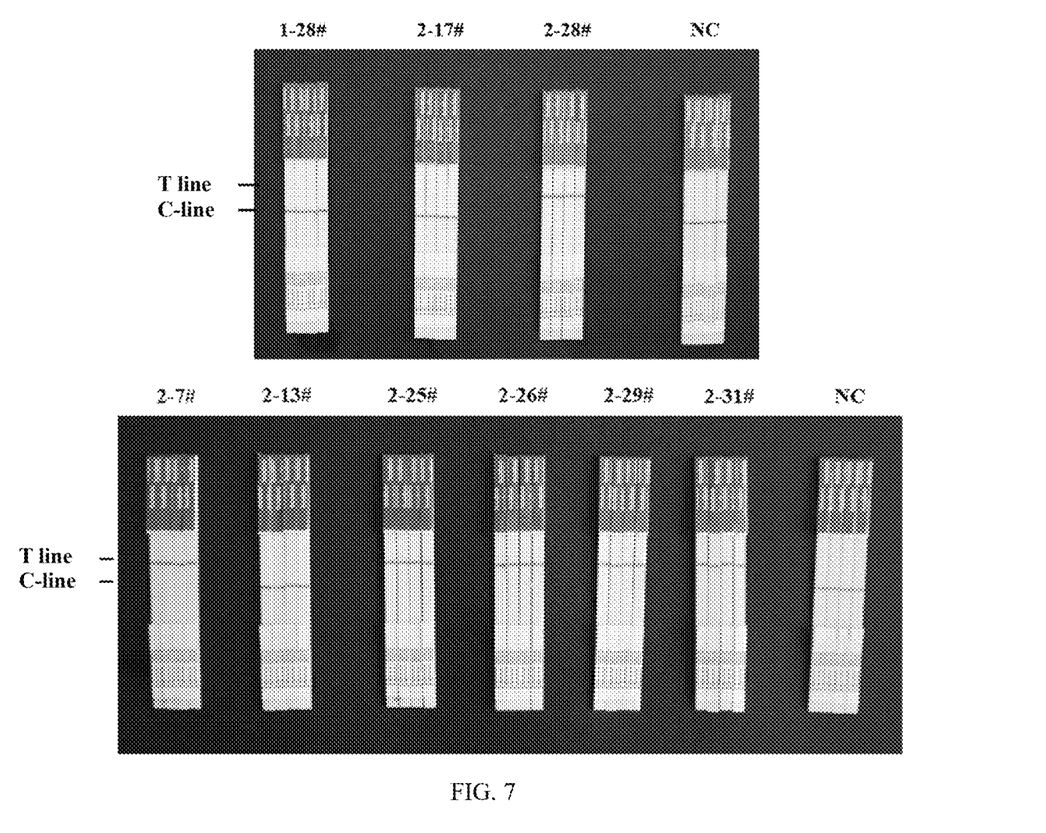
FIG. 7 shows the results of screening CD71 gene edited cells from monoclonal cells by crRNA-F3 colloidal gold test strip system in Example 3 of the present invention.

Results were shown in FIG. 7, the T-lines of 2-28 #, 2-7 #, 2-25 #, 2-26 #, 2-29 #, and 2-31 #showed coloration (positive), indicating that they were not CD71 gene bi-allelic gene edited cells; the T-lines of 1-28 #, 2-17 #, and 2-13 #did not show coloration (negative), they were CD71 gene bi-allelic gene edited cells.

The above results indicated that both the crRNA-F3 fluorescence detection system and the colloidal gold strip detection system could detect nucleic acid samples containing a wild-type sequence of CD71 gene (SEQ ID NO: 7), which can be used to screen CRISPR/Cas9 induced CD71 gene bi-allelic gene edited monoclonal cells.

In order to determine the accuracy and specificity of a method for rapidly detecting CRISPR/Cas9 induced bi-allelic gene edited cells provided by the present invention, the genotype of the selected biallelic gene edited cells were identified by TA cloning using the PCR products of each monoclonal cell.

Figure 8:
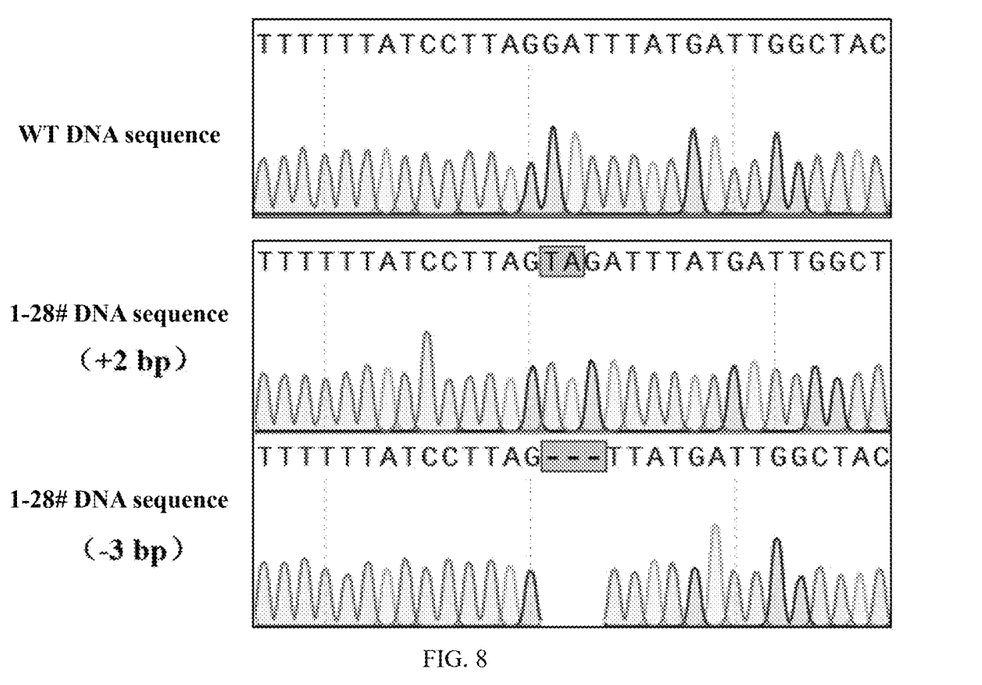
FIG. 8 shows the TA cloning results of bi-allelic gene edited cells of CRISPR/Cas9 induced sgRNA editing site in Example 3 of the present invention, including TTTTT-TATCCTTAGTAGATTTATGATTGGCT shown in SEQ ID NO: 19, TTTTTTATCCTTAGTTATGATTGGCTAC shown in SEQ ID NO: 20.

Partial sequencing results were shown in FIG. 8. 1-28 #are CD71 gene bi-allelic gene edited cells, and the target sequences of their two homologous chromosomes are shown in FIG. 8. As can be seen, the target (SEQ ID NO: 7) in CD71 on both homologous chromosomes of 1-28 #has undergone mutations compared with the target (SEQ ID NO: 7) in the wild-type CD71, with one homologous chromosome having a 2 bp insertion and the other homologous chromosome having a 3 bp deletion. Therefore, 1-28 #are CD71 gene bi-allelic gene edited cells, which is consistent with the screening results of crRNA-F3 nucleic acid detection system.

The sequencing results of other CD71 gene bi-allelic gene edited cells also showed that the target (SEQ ID NO: 7) in CD71 on both homologous chromosomes had mutations, consistent with the screening results of crRNA-F3 nucleic acid detection system.

The sequencing results of cells that were not CD71 gene bi-allelic gene edited cells also showed that the target (SEQ ID NO: 7) in CD71 on both homologous chromosomes had no mutation, consistent with the screening results of the crRNA-F3 nucleic acid detection system.

This result demonstrates that crRNA-F3 can be used for specific screening of CD71 gene bi-allelic gene edited samples with extremely high accuracy.

Example 4: Sensitivity Test of crRNA-F3 Nucleic Acid Detection System

Wild-type standard plasmid pClone EZ-TOPO-WT of pig CD71 gene was diluted with ddH2O gradient without nuclease to concentrations of $3.71 \times 10^{10}$, $3.71 \times 10^{9}$, $3.71 \times 10^{8}$, $3.71 \times 10^{7}$, $3.71 \times 10^{6}$, $3.71 \times 10^{5}$, $3.71 \times 10^{4}$, $3.71 \times 10^{3}$, $3.71 \times 10^{2}$, $3.71 \times 10^{1}$, and $3.71 \times 10^{0}$ copies/µL, respectively.

The pClone EZ-TOPO-WT plasmids with gradient concentrations were used as a DNA template for detection according to CRISPR/Cas12a fluorescence detection in 2 of Example 2.

Figure 9:
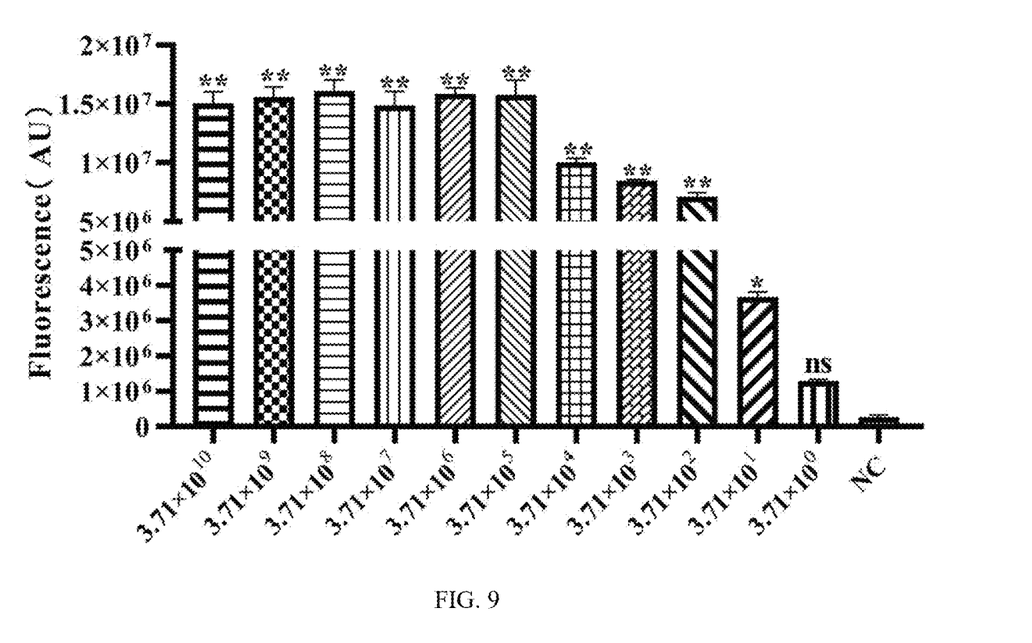
FIG. 9 shows the sensitivity test results of the crRNA-F3 system in Example 4 of the present invention. ** indicates highly significant difference (P<0.01) compared to the negative control group, * indicates significant difference (P<0.05) compared to the negative control group, ns indicates no significant difference (P>0.05) compared to the negative control group.

The detection results were shown in FIG. 9, showing that in the Cas12a system involving crRNA-F3, when a concentration of the standard plasmid was $3.71 \times 10^{1}$ copies/µL or above, the fluorescence signal intensity was significantly higher or extremely significantly higher than that of the negative control group (P<0.05, P<0.01), indicating that the standard plasmid at a concentration of $3.71 \times 10^{1}$ copies/µL is the minimum detection sensitivity of the crRNA-F3 detection system.

This result indicated that the system still has good detection capacity and higher sensitivity under extremely low concentration conditions.

Therefore, the crRNA-F3 nucleic acid detection system provided by the present invention can quickly screen for CD71 gene bi-allelic gene edited cells that meet expectations in a short period of time, which plays an important role in accelerating the development of CD71 gene functional analysis.

The present invention has been described in detail as above. For those skilled in the art, the present invention can be implemented within a wide range under equivalent parameters, concentrations, and conditions without departing from the purpose and scope of the present invention, and without the need for unnecessary experiments. Although the present invention provides specific examples, it should be understood that further improvements can be made to the present invention. In summary, according to the principles of the present invention, this application is intended to include any modifications, uses, or improvements to the present invention, including changes made using conventional techniques known in the art that depart from the scope already disclosed in this application. According to the scope of the attached claims, some basic features can be applied.

What is claimed is:

1. A clustered regularly interspaced short palindromic repeats (CRISPR) ribonucleic acid (crRNA), wherein the nucleotide sequence of the crRNA is SEQ ID NO: 6, and the crRNA binds to a target.

2. The crRNA according to claim 1, wherein the crRNA is transcribed from a transcription template in vitro; and
   the transcription template is a product obtained by annealing the single stranded DNA molecule shown in SEQ ID NO: 10 and the single stranded DNA molecule shown in SEQ ID NO: 13.

3. The crRNA according to claim 1, wherein the nucleotide sequence of the crRNA is selected from SEQ ID NO: 14, SEQ ID NO: 15, or SEQ ID NO: 16.

4. A product, comprising the crRNA according to claim 1.

5. The product according to claim 4, further comprising a CRISPR-associated protein 12a (Cas12a) protein.

6. The product according to claim 5, further comprising a primer pair for specifically amplifying the target; wherein the primer pair comprises the single stranded DNA molecule comprising SEQ ID NO: 2 and the single stranded DNA molecule comprising SEQ ID NO: 3.

7. The product according to claim 6, further comprising a single stranded DNA probe, wherein the single stranded DNA probe is labeled with different groups on both ends, respectively;
   and/or the different groups comprise fluorescent groups, quenching groups, and/or a biotin.

8. The product according to claim 4, further comprising a kit, a test strip, or a fluorescence detection system.

9. A substance, comprising:
   A1) the Cas12a protein and the crRNA according to claim 5, or a complex formed by the Cas12a protein and the crRNA; or
   A2) a primer pair for amplifying the target, wherein the primer pair comprises the single stranded DNA molecule comprising SEQ ID NO: 2 and the single stranded DNA molecule comprising SEQ ID NO: 3.

10. A method for detecting or assisting bi-allelic gene edited samples of a CD71 gene, comprising the following steps:
    C1) performing a polymerase chain reaction (PCR) amplification using a nucleic acid of a sample to be tested as a template, and a primer pair comprising the single stranded DNA molecule comprising SEQ ID NO: 2 and the single stranded DNA molecule comprising SEQ ID NO: 3 to obtain a PCR product;
    C2) preparing a CRISPR/Cas12a fluorescence detection system or a CRISPR/Cas12a colloidal gold test strip detection system comprising the following components: the PCR product, a Cas12a protein, the crRNA in the product according to claim 4, and a single stranded DNA probe, or a CRISPR-Cas12a; and
    C3) reacting the CRISPR/Cas12a fluorescence detection system and detecting reaction products to identify whether the sample to be tested is the bi-allelic gene edited samples of the CD71 gene;
    wherein the product further comprises the Cas12a protein, a primer pair for amplifying the target, and the single stranded DNA probe, wherein the primer pair comprises the single stranded DNA molecule comprising SEQ ID NO: 2 and the single stranded DNA molecule comprising SEQ ID NO: 3, the single stranded DNA probe is labeled with different groups on both ends, respectively; and/or the different groups comprise fluorescent groups, quenching groups, and/or a biotin.

11. The method according to claim 10, wherein the crRNA is transcribed from a transcription template in vitro;
    the transcription template is a product obtained by annealing the single stranded DNA molecule shown in SEQ ID NO: 10 and the single stranded DNA molecule shown in SEQ ID NO: 13.

12. The method according to claim 10, wherein the crRNA has the nucleotide sequence selected from SEQ ID NO: 14, SEQ ID NO: 15, or SEQ ID NO: 16.

13. The method according to claim 10, wherein the sample to be tested is a cell or an organism.

14. The method according to claim 13, wherein the cell comprises a cell with a CD71 gene edited, a cell with a wild-type CD71 gene, a CD71 gene mono-allelic gene edited cell, and a CD71 gene bi-allelic gene edited cell.

15. The method according to claim 10, wherein the single stranded DNA probe is a single stranded DNA with a length of 5-50 nt and rich in AT bases.

16. The method according to claim 14, wherein the crRNA is transcribed from a transcription template in vitro;
    the transcription template is a product obtained by annealing the single stranded DNA molecule shown in SEQ ID NO: 10 and the single stranded DNA molecule shown in SEQ ID NO: 13.

17. The product according to claim 7, wherein the single stranded DNA probe in a CRISPR/Cas12a fluorescence detection system is 6-FAM-TTATT-BHQ1; and the single stranded DNA probe in a CRISPR/Cas12a colloidal gold test strip detection system is 6-FAM-TTTTTTTATTTTTT (SEQ ID NO: 17)-C6Biotin.

18. The product according to claim 7, wherein the single stranded DNA probe is a single stranded DNA with a length of 5-50 nt and rich in AT bases.

* * * * *

SEQUENCE LISTING

```
Sequence total quantity: 22
SEQ ID NO: 1              moltype = DNA  length = 20
FEATURE                   Location/Qualifiers
source                    1..20
                          mol_type = other DNA
                          organism = synthetic construct
SEQUENCE: 1
```

```
gtagccaatc ataaatccta                                          20

SEQ ID NO: 2            moltype = DNA   length = 19
FEATURE                 Location/Qualifiers
source                  1..19
                        mol_type = other DNA
                        organism = synthetic construct
SEQUENCE: 2
tgaggattca aggtaggct                                           19

SEQ ID NO: 3            moltype = DNA   length = 19
FEATURE                 Location/Qualifiers
source                  1..19
                        mol_type = other DNA
                        organism = synthetic construct
SEQUENCE: 3
ctgatgccct tgtggatag                                           19

SEQ ID NO: 4            moltype = DNA   length = 24
FEATURE                 Location/Qualifiers
source                  1..24
                        mol_type = other DNA
                        organism = synthetic construct
SEQUENCE: 4
tttatcctta ggatttatga ttgg                                     24

SEQ ID NO: 5            moltype = DNA   length = 23
FEATURE                 Location/Qualifiers
source                  1..23
                        mol_type = other DNA
                        organism = synthetic construct
SEQUENCE: 5
tttttatcc ttaggattta tga                                       23

SEQ ID NO: 6            moltype = DNA   length = 27
FEATURE                 Location/Qualifiers
source                  1..27
                        mol_type = other DNA
                        organism = synthetic construct
SEQUENCE: 6
tttttatcc ttaggattta tgattgg                                   27

SEQ ID NO: 7            moltype = DNA   length = 31
FEATURE                 Location/Qualifiers
source                  1..31
                        mol_type = other DNA
                        organism = synthetic construct
SEQUENCE: 7
tttttatcc ttaggattta tgattggcta c                              31

SEQ ID NO: 8            moltype = DNA   length = 61
FEATURE                 Location/Qualifiers
source                  1..61
                        mol_type = other DNA
                        organism = synthetic construct
SEQUENCE: 8
taatacgact cactataggg taatttctac taagtgtaga ttccttagga tttatgattg 60
g                                                              61

SEQ ID NO: 9            moltype = DNA   length = 61
FEATURE                 Location/Qualifiers
source                  1..61
                        mol_type = other DNA
                        organism = synthetic construct
SEQUENCE: 9
taatacgact cactataggg taatttctac taagtgtaga ttttatcctt aggatttatg 60
a                                                              61

SEQ ID NO: 10           moltype = DNA   length = 64
FEATURE                 Location/Qualifiers
source                  1..64
                        mol_type = other DNA
                        organism = synthetic construct
SEQUENCE: 10
taatacgact cactataggg taatttctac taagtgtaga tttatcctta ggatttatga 60
ttgg                                                           64

SEQ ID NO: 11           moltype = DNA   length = 61
FEATURE                 Location/Qualifiers
```

```
source                  1..61
                        mol_type = other DNA
                        organism = synthetic construct
SEQUENCE: 11
ccaatcataa atcctaagga atctacactt agtagaaatt accctatagt gagtcgtatt    60
a                                                                    61

SEQ ID NO: 12           moltype = DNA  length = 61
FEATURE                 Location/Qualifiers
source                  1..61
                        mol_type = other DNA
                        organism = synthetic construct
SEQUENCE: 12
tcataaatcc taaggataaa atctacactt agtagaaatt accctatagt gagtcgtatt    60
a                                                                    61

SEQ ID NO: 13           moltype = DNA  length = 64
FEATURE                 Location/Qualifiers
source                  1..64
                        mol_type = other DNA
                        organism = synthetic construct
SEQUENCE: 13
ccaatcataa atcctaagga taaatctaca cttagtagaa attaccctat agtgagtcgt    60
atta                                                                 64

SEQ ID NO: 14           moltype = RNA  length = 41
FEATURE                 Location/Qualifiers
source                  1..41
                        mol_type = other RNA
                        organism = synthetic construct
SEQUENCE: 14
taatttctac taagtgtaga ttccttagga tttatgattg g                        41

SEQ ID NO: 15           moltype = RNA  length = 41
FEATURE                 Location/Qualifiers
source                  1..41
                        mol_type = other RNA
                        organism = synthetic construct
SEQUENCE: 15
taatttctac taagtgtaga ttttatcctt aggatttatg a                        41

SEQ ID NO: 16           moltype = RNA  length = 44
FEATURE                 Location/Qualifiers
source                  1..44
                        mol_type = other RNA
                        organism = synthetic construct
SEQUENCE: 16
taatttctac taagtgtaga tttatcctta ggatttatga ttgg                     44

SEQ ID NO: 17           moltype = DNA  length = 15
FEATURE                 Location/Qualifiers
source                  1..15
                        mol_type = other DNA
                        organism = synthetic construct
SEQUENCE: 17
tttttttatt ttttt                                                     15

SEQ ID NO: 18           moltype = DNA  length = 40
FEATURE                 Location/Qualifiers
source                  1..40
                        mol_type = other DNA
                        organism = synthetic construct
SEQUENCE: 18
tttttatcct taggatttat gattggctac ttggcctatt                          40

SEQ ID NO: 19           moltype = DNA  length = 31
FEATURE                 Location/Qualifiers
source                  1..31
                        mol_type = other DNA
                        organism = synthetic construct
SEQUENCE: 19
tttttatcc ttagtagatt tatgattggc t                                    31

SEQ ID NO: 20           moltype = DNA  length = 28
FEATURE                 Location/Qualifiers
source                  1..28
                        mol_type = other DNA
                        organism = synthetic construct
SEQUENCE: 20
```

```
tttttatcc ttagttatga ttggctac                                               28

SEQ ID NO: 21           moltype = DNA  length = 20
FEATURE                 Location/Qualifiers
source                  1..20
                        mol_type = other DNA
                        organism = synthetic construct
SEQUENCE: 21
taatacgact cactataggg                                                       20

SEQ ID NO: 22           moltype = DNA  length = 21
FEATURE                 Location/Qualifiers
source                  1..21
                        mol_type = other DNA
                        organism = synthetic construct
SEQUENCE: 22
taatttctac taagtgtaga t                                                     21
```